United States Patent [19]

Sawa et al.

[11] 4,148,211

[45] Apr. 10, 1979

[54] SAMPLING SYSTEM FOR ENGINE EXHAUST GAS ANALYSIS APPARATUS

[75] Inventors: Kenneth B. Sawa, Yorba Linda; Willis M. Peek; John D. Blanke, both of Fullerton, all of Calif.

[73] Assignee: Beckman Instruments, Inc., Fullerton, Calif.

[21] Appl. No.: 889,452

[22] Filed: Mar. 22, 1978

[51] Int. Cl.² ............................................. G01N 27/50
[52] U.S. Cl. ...................................... 73/23; 204/195 P
[58] Field of Search ................ 73/23, 421.5; 204/1 Y, 204/195 P

[56] References Cited

U.S. PATENT DOCUMENTS

| | | | |
|---|---|---|---|
| 3,822,581 | 7/1974 | Hauk | 73/23 |
| 3,917,454 | 11/1975 | Clark | 73/23 |
| 3,948,081 | 4/1976 | Wessel et al. | 73/23 |

Primary Examiner—S. Clement Swisher
Attorney, Agent, or Firm—R. J. Steinmeyer; P. R. Harder; F. J. Kowalski

[57] ABSTRACT

In apparatus for analyzing the exhaust gas of a motor vehicle, the apparatus including an oxygen sensor and means for sampling a portion of the exhaust gas and conducting the sample to the sensor, there is disclosed an improvement wherein the exhaust gas is used to heat a moisture barrier and the oxygen sensor and is then cooled before being directed through the moisture barrier to the sensitive area of the oxygen sensor. This arrangement prevents moisture from condensing on the sensitive area of the oxygen sensor, which moisture would interfere with the operation of the sensor.

8 Claims, 4 Drawing Figures

U.S. Patent  Apr. 10, 1979  4,148,211
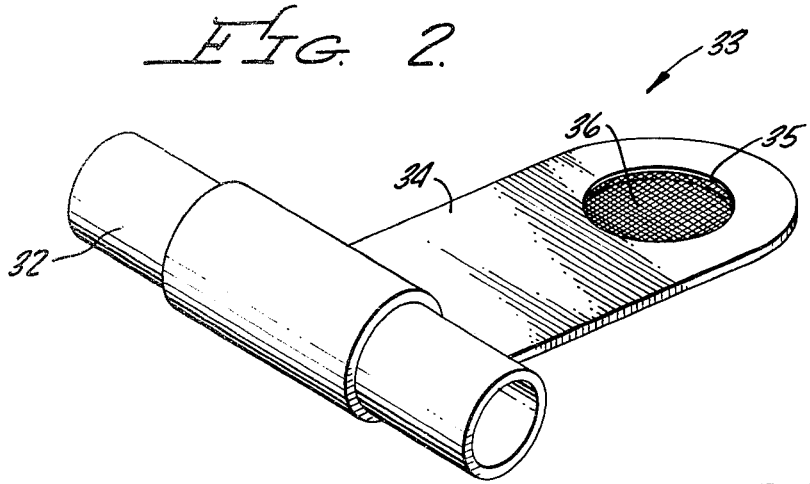
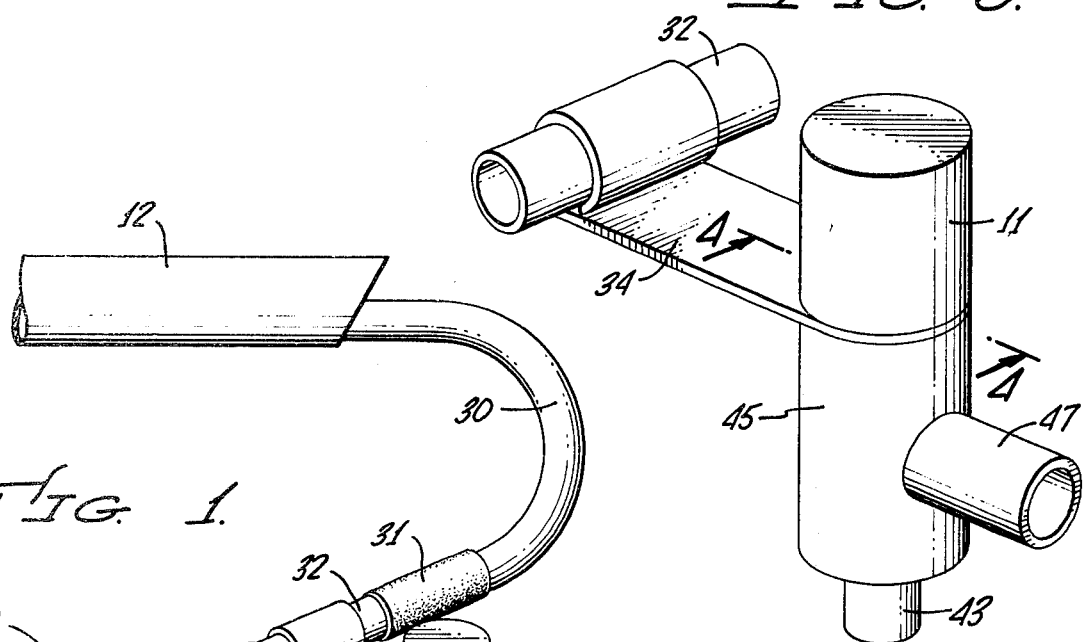
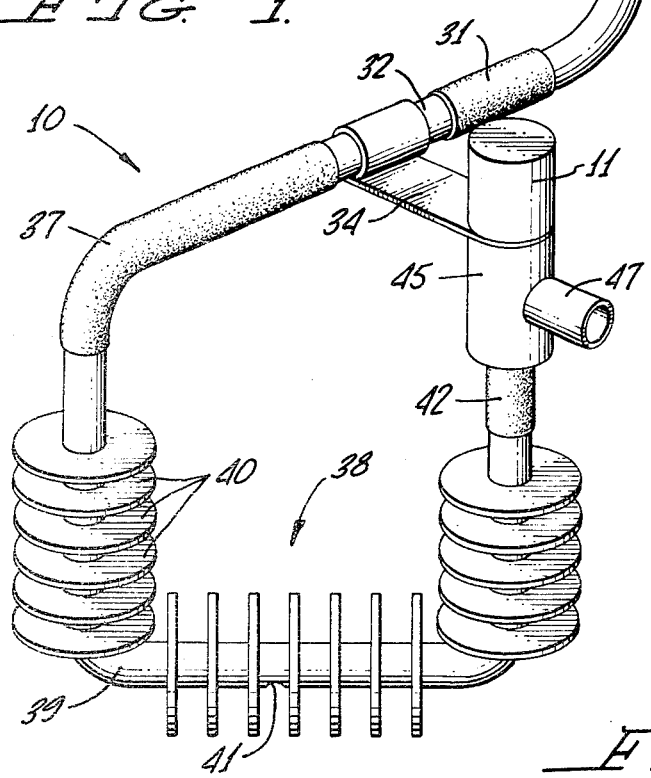
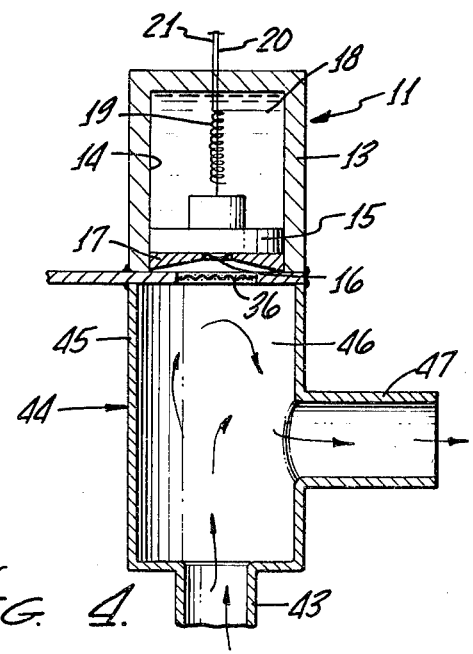

SAMPLING SYSTEM FOR ENGINE EXHAUST GAS ANALYSIS APPARATUS

BACKGROUND OF THE INVENTION

1. Field of the Invention

The present invention relates to a sampling system for engine exhaust gas analysis apparatus and, more particularly, to such a system which eliminates the condensation of moisture on the sensitive area of an oxygen sensor used therein.

2. Description of the Prior Art

It has been found that an oxygen analyzer can be combined with an HC/CO analyzer to provide significant information when analyzing the exhaust gas of a motor vehicle for engine diagnostic purposes. Excess oxygen in the exhaust gas of motor vehicles with catalytic converters has been identified as a major cause of increased sulfate emissions. The presence of increasing levels (spiking) of oxygen in the exhaust gas of motor vehicles is often the result of intermittent misfire or "lean roll." This condition can be detected by sampling a portion of the exhaust gas from the automotive vehicle and conducting the sample to an oxygen sensor. By coupling the sensor with means for differentiating the signal output thereof, both the quantity and rate of change of oxygen in the exhaust gas is available. Apparatus can then be provided for indicating and/or alarming quantity and rate of change values outside preset limits. A technician can then use this information to adjust the idle mixture of an automobile engine to prevent a lean roll.

Engine exhaust gas analysis apparatus including an oxygen sensor and means for sampling a portion of the exhaust gas and conducting the sample to the sensor is disclosed in U.S. Pat. No. 4,030,349, assigned to the assignee of the present application. In such patent, an oxygen sensor connected to a probe is inserted into the exhaust pipe of an automobile to conduct a portion of the exhaust gas to the sensor. The oxygen sensor generally comprises a pair of electrodes mounted within a body and electrically connected by an electrolyte and separated from the exhaust gas sample by means of a membrane that is permeable to oxygen, but impermeable to the electrolyte.

As the exhaust gas sample is brought into contact with the membrane, oxygen diffuses through the membrane to contact one of the electrodes in the presence of the electrolyte. A current flow results which is linear with the partial pressure of oxygen being sampled. Thus, the current can be measured and correlated to the amount of oxygen in the sample. Such sensors are quite rapid, simple in operation, and especially suited for determining either gaseous or dissolved oxygen in liquids or gases.

The exhaust gas from a motor vehicle is quite hot, typically in the range of 350°-500° F. In addition, such exhaust gas is relatively high in humidity, typically containing 12-16% $H_2O$. When the hot exhaust gas impinges on the cold oxygen sensor, the moisture therein condenses, often coating the sensitive area of the sensor. This has been found to mask the changes in the oxygen concentration in the sample, substantially reducing the effectiveness of such exhaust gas analysis apparatus.

SUMMARY OF THE INVENTION

According to the present invention, this problem is solved by the provision of a novel sampling system for engine exhaust gas analysis apparatus. With the inclusion of the present sampling system, the engine analysis apparatus operates economically, efficiently, and rapidly by eliminating the condensation of moisture on the sensitive area of the oxygen sensor. This is achieved by utilizing the hot exhaust gas to heat the sensor and a moisture shield on which the sensor is mounted. The exhaust gas is then cooled before being conducted through the moisture shield onto the sensitive area of the sensor. Since the moisture shield and the sensor are now hotter than the exhaust gas impinging thereon, moisture does not condense on the sensitive area of the sensor.

Briefly, in apparatus for analyzing the exhaust gas of a motor vehicle, the apparatus including an oxygen sensor and means for sampling a portion of the exhaust gas and conducting the sample to the sensor, there is disclosed an improvement which prevents moisture from condensing on the sensor wherein the conducting means comprises a first heat exchanger, the oxygen sensor being mounted on the first heat exchanger, a first conduit for conducting the exhaust gas portion to the first heat exchanger for heating the same and the sensor mounted thereon, a second heat exchanger for cooling exhaust gases, a second conduit for conducting the exhaust gas portion from the first heat exchanger to the second heat exchanger for cooling same, and a third conduit for conducting the cooled exhaust gas portion from the second heat exchanger to the oxygen sensor.

It is therefore an object of the present invention to provide a sampling system for engine exhaust gas analysis apparatus.

It is a further object of the present invention to provide a sampling system for engine exhaust gas analysis apparatus including a sensor which prevents moisture from condensing on the sensor.

It is a still further object of the present invention to provide a sampling system for engine exhaust gas analysis apparatus including a sensor which utilizes the exhaust gas to heat the sensor.

Still other objects, features, and attendant advantages of the present invention will become apparent to those skilled in the art from a reading of the following detailed description of the preferred embodiment constructed in accordance therewith, taken in conjunction with the accompanying drawings wherein like numerals designate like parts in the several figures and wherein:

BRIEF DESCRIPTION OF THE DRAWINGS

FIG. 1 is a perspective view of a sampling system for engine exhaust gas analysis apparatus constructed in accordance with the teachings of the present invention;

FIG. 2 is an enlarged perspective view of the first heat exchanger of the system of FIG. 1;

FIG. 3 is an enlarged perspective view of a portion of the apparatus of FIG. 1; and FIG. 4 is a sectional view taken along the line 4—4 in FIG. 3.

DESCRIPTION OF THE PREFERRED EMBODIMENT

Referring now to the drawings and, more particularly, to FIG. 1 thereof, the present sampling system, generally designated 10, is adapted for use in engine exhaust gas analysis apparatus of the type including a sensor 11 adapted to receive a portion of the exhaust gas emanating from the exhaust pipe 12 of an automobile (not shown). Such a sampling system could be used in apparatus of the type disclosed in U.S. Pat. No. 4,030,349. In such apparatus, sensor 11 is an oxygen sensor. However, it will be apparent to those skilled in the art that sensor 11 could be an HC sensor, a CO sensor, an $NO_x$ sensor, or any other type of sensor useful in exhaust gas diagnostic apparatus. Therefore, while an oxygen sensor will be described, the teachings of the present invention are not so limited.

Referring now to FIG. 4, there is shown a highly simplified construction of a generally conventional amperometric oxygen sensor 11 including a body 13 defining an enclosure 14. Mounted within enclosure 14 is a support member 15 for supporting a cathode electrode (not shown). A membrane (not shown) is stretched across an opening 16 in a cap 17 positioned in the open end of body 11 and the perimeter of the membrane is connected to body 13. Enclosure 14 is filld with an electrolyte 18. An anode 19 is disposed within enclosure 14 in contact with electrolyte 18. Electrical leads 20 and 21 connected to the cathode and anode 19, respectively, extend from body 13 for connection to a voltage source (not shown)

In forming such a sensor for use as an amperometric oxygen sensor, the cathode is typcially made from gold, anode 19 is typically made from silver, the membrane is typically made from polytetrafluoroethylene, and electrolyte 18 is typically a 5% KCl solution, either buffered or unbuffered. A potential of 750 millivolts is typically applied between the cathode and anode 19. As a sample is brought in contact with the membrane through opening 16 in cap 17, oxygen from the sample diffuses through the membrane and is reduced at the cathode. A current flows which is linear with the partial pressure of oxygen being sampled. This current can be measured and correlated to the amount of oxygen in the sample.

The ability of sensor 11 to operate properly is adversely affected by moisture condensing on the vicinity of opening 16 in cap 17. This has occurred commonly heretofore since the gas emanating from exhaust pipe 12 typically has a temperature in the range of 350°–500° F. and is high in humidity, typically containing 12–16% $H_2O$.

Referring now to FIGS. 1–4, sampling system 10 includes a first conduit, preferably a length of large diameter tubing 30, one end of which extends into the open end of exhaust pipe 12. This allows the pressure inside of exhaust pipe 12 to force the exhaust through sampling system 10 without the use of a separate pump. The other end of tubing 30 is connected via a length of flexible hose 31 to one end of a length of tubing 32 which is part of a heat exchanger, generally designated 33, which is constructed entirely from heat conducting material, such as copper. Heat exchanger 33 also includes a plate 34, one end of which is connected to tubing 32, such as by being wrapped therearound, as shown. Plate 34 has a hole 35 therein which is approximately equal to or slightly larger than hole 16 in cap 17 of sensor 11. A fine mesh screen 36 of heat conducting material is positioned in hole 35. As shown in FIGS. 1, 3, and 4, sensor 11 is mounted on one side of plate 34 so that opening 16 is facing screen 36.

The other end of tubing 32 is connected by a second conduit, preferably a length of flexible hose 37, to one end of a second heat exchanger, generally designated 38. Heat exchanger 38 is a condensor which may consist of a length of metallic tubing 39 having a plurality of fins 40 mounted thereon. A drain hole 41 is positioned in tubing 39, at the lowest point therein.

Heat exchanger 38 is also connected by a third conduit, preferably a length of flexible hose 42, to the inlet 43 of a housing 44. Housing 44 includes a body 45 defining a chamber 46. Inlet 43 enters body 45 from one end thereof and the other end thereof is open and connected to the other side of plate 34, surrounding screen 36. Body 45 has an outlet 47 in the side thereof.

In operation, tubing 30 and hose 31 conduct the hot exhaust gas from exhaust pipe 12 through tubing 32. Since tubing 32 and the remainder of heat exchanger 33 are made from a thermally conductive material, such as copper, the hot exhaust gas heats tubing 32, plate 34, and screen 36, and also heats sensor 11 mounted thereon. After passing through tubing 32, the hot exhaust gas sample is conducted by hose 37 through condensor 38 where the exhaust gas sample is substantially cooled. The length of tubing 39 and the material used are selected such that the exhaust gas temperature has been dropped to approximately 30° F. above ambient temperature by the time it reaches hose 42. The cooled exhaust gas then enters chamber 46 where it passes through screen 36 and impinges on the sensitive area of sensor 11. The exhaust gas then exits through outlet 47 of housing 44 where it may be vented to the atmosphere.

Screen 36 operates at two different levels. Initially, when tubing 30 is first placed into the end of exhaust pipe 12, all of the elements of sampling system 10 are cold, including screen 36. As a result, when the hot exhaust gas entering chamber 46 impinges on screen 36, moisture condenses on screen 36 rather than on the sensitive area of sensor 11. As the exhaust gas continues to flow, tubing 32, plate 34, and screen 36 are heated, creating a thermal plane which is some number of degrees warmer than the temperature of the same exhaust gas impinging thereon after it has passed through condensor 38. As a result, the moisture previously condensed on screen 36 evaporates and passes with the exhaust gas out of outlet 47 of housing 45. Thereafter, this thermal plane acts as a moisture shield and is effective in preventing further condensation from forming on or near sensor 11.

As shown in FIG. 1, the entire system should slope downwardly to condensor 38 so that the water condensing in any of the lines drains to the lowest point in system 10, where drain hole 41 is located.

While the invention has been described with respect to a preferred physical embodiment constructed in accordance therewith, it will be apparent to those skilled in the art that various modifications and improvements may be made without departing from the scope and spirit of the invention. Accordingly, it is to be understood that the invention is not to be limited by the specific illustrative embodiment, but only by the scope of the appended claims.

We claim:

1. In apparatus for analyzing the exhaust gas of a motor vehicle, said apparatus including a gas sensor and means for sampling a portion of said exhaust gas and conducting said portion to said sensor, the improvement wherein said conducting means comprises:
   first heat exchange means, said sensor being mounted on said first heat exchange means;

first conduit means for conducting said exhaust gas portion to said first heat exchange means for heating same and said sensor mounted thereon;

second heat exchange means for cooling exhaust gases;

second conduit means for conducting said exhaust gas portion from said first heat exchange means to said second heat exchange means for cooling same; and third conduit means for conducting said cooled exhaust gas portion from said second heat exchange means to said sensor.

2. In apparatus according to claim 1, the improvement wherein said first heat exchange means comprises:

a tube of heat conducting material, said exhaust gas portion being conducted through said tube; and a plate of heat conducting material, one end of said plate being connected to said tube, said plate having a hole therein of a size which matches the sensitive area of said sensor, said sensor being mounted on one side of said plate with the sensitive area thereof aligned with said hole therein.

3. In apparatus according to claim 2, the improvement wherein said third conduit means causes said cooled exhaust gas portion to impinge on the other side of said plate, in the vicinity of said hole therein.

4. In apparatus according to claim 2 or 3, the improvement wherein said first heat exchange means further comprises:

a screen of heat conducting material extending across said hole in said plate.

5. In apparatus according to claim 4, the improvement wherein said second heat exchange means comprises:

a condensor.

6. In apparatus according to claims 1, 2, or 3, wherein said motor vehicle includes an exhaust pipe, the improvement wherein one end of said first conduit means extends into the open end of said motor vehicle exhaust pipe and has a diameter sufficient to allow the pressure inside of said exhaust pipe to force said exhaust gas sample through aid conducting means to said sensor.

7. In apparatus for analyzing the exhaust gas of a motor vehicle, said apparatus including a gas sensor and means for sampling a portion of said exhaust gas and conducting said sample to said sensor, a method for preventing moisture from condensing on said sensor comprising the steps of:

utilizing said exhaust gas portion to heat a moisture shield on which said sensor is mounted;

subsequently cooling aid exhaust gas portion to a temperature below that of said moisture shield; and conducting said exhaust gas portion through said moisture shield to the sensitive area of said sensor.

8. In apparatus according to claim 7, a method wherein said step of utilizing said exhaust gas portion to heat said moisture shield also utilizes said exhaust gas portion to heat said sensor.

* * * * *

UNITED STATES PATENT AND TRADEMARK OFFICE
CERTIFICATE OF CORRECTION

PATENT NO. : 4,148,211
DATED : April 10, 1979
INVENTOR(S) : Kenneth B. Sawa, Willis M. Peek and John D. Blanke It is certified that error appears in the above–identified patent and that said Letters Patent are hereby corrected as shown below:

Column 6, line 13   "aid" should be deleted and the word --said-- should be inserted.

Signed and Sealed this

Twenty-sixth Day of February 1980

[SEAL]

Attest:

SIDNEY A. DIAMOND

*Attesting Officer*   *Commissioner of Patents and Trademarks*